United States Patent
Schildbach et al.

(10) Patent No.: US 7,939,618 B2
(45) Date of Patent: May 10, 2011

(54) PROCESS FOR THE CONTINUOUS PREPARATION OF ORGANOPOLYSILOXANES HAVING AMINOALKYL GROUPS

(75) Inventors: Daniel Schildbach, Neuoetting (DE); Johann Bindl, Burghausen (DE); Gilbert Geisberger, Altoetting (DE)

(73) Assignee: Wacker Chemie AG, Munich (DE)

( * ) Notice: Subject to any disclaimer, the term of this patent is extended or adjusted under 35 U.S.C. 154(b) by 313 days.

(21) Appl. No.: 12/111,293

(22) Filed: Apr. 29, 2008

(65) Prior Publication Data

US 2008/0275194 A1 Nov. 6, 2008

(30) Foreign Application Priority Data

May 2, 2007 (DE) .......... 10 2007 020 568

(51) Int. Cl.
  *C08G 77/26* (2006.01)
(52) U.S. Cl. .............. 528/38; 528/34; 526/64
(58) Field of Classification Search .......... 528/38, 528/34; 526/64
  See application file for complete search history.

(56) References Cited

U.S. PATENT DOCUMENTS

| | | | |
|---|---|---|---|
| 3,853,934 A | 12/1974 | Siciliano et al. | |
| 4,128,568 A | 12/1978 | Buechner et al. | |
| 4,250,290 A | 2/1981 | Petersen | |
| 4,565,889 A * | 1/1986 | Livingston et al. | 564/205 |
| 4,652,662 A | 3/1987 | Von Au et al. | |
| 5,077,421 A | 12/1991 | Selvig | |
| 5,456,888 A | 10/1995 | Gilson et al. | |
| 6,350,824 B1 | 2/2002 | Baumann et al. | |
| 6,441,105 B2 * | 8/2002 | Naganawa et al. | 525/477 |
| 6,964,753 B2 * | 11/2005 | Gilson | 422/108 |
| 7,129,369 B2 | 10/2006 | Heller et al. | |
| 2005/0119434 A1 | 6/2005 | Chayama et al. | |
| 2005/0215806 A1 * | 9/2005 | Heller et al. | 556/413 |
| 2007/0197757 A1 | 8/2007 | Schaefer et al. | |

FOREIGN PATENT DOCUMENTS

| | | |
|---|---|---|
| CN | 1673256 A | 9/2005 |
| DE | 2 705 563 A | 8/1978 |
| DE | 3 418 358 A | 11/1985 |
| EP | 0 522 776 A1 | 1/1993 |
| EP | 0950680 A | 10/1999 |
| EP | 0 982 347 A1 | 3/2000 |
| EP | 1175937 A | 1/2002 |
| EP | 1 580 215 A | 9/2005 |
| EP | 1580215 A | 9/2005 |
| JP | 11322943 A | 11/1999 |
| JP | 2005272842 A | 10/2005 |
| WO | 2005/087842 A1 | 9/2005 |

* cited by examiner

Primary Examiner — Kuo-Liang Peng
(74) Attorney, Agent, or Firm — Brooks Kushman P.C.

(57) ABSTRACT

Organopolysiloxanes having aminoalkyl groups are prepared by
(i) reacting
  (A) linear, cyclic or branched organopolysiloxanes with
  (B) aminoalkylsilanes which have an SiC-bonded, basic nitrogen-containing hydrocarbon radical and 2 or 3 hydrolyzable groups,
    or the partial or complete hydrolysis products thereof, optionally in the presence of
  (C) basic catalysts and/or
  (D) chain-terminating reagents, and
(ii) optionally, after the reaction (i) neutralizing the optionally used basic catalysts (c),
with the proviso that compounds (A), (B) and, when used, (D) are reacted continuously in a reaction space whose ratio of length to diameter is equal to or greater than four.

16 Claims, 1 Drawing Sheet

PROCESS FOR THE CONTINUOUS PREPARATION OF ORGANOPOLYSILOXANES HAVING AMINOALKYL GROUPS

BACKGROUND OF THE INVENTION

1. Field of the Invention

The invention relates to a process for the preparation of organopolysiloxanes having aminoalkyl groups.

2. Background Art

Organopolysiloxanes carrying aminoalkyl groups, referred to below as amine oils, are among the most important organically functionalized organopolysiloxanes and are successfully used in many different applications. These include, inter alia, textile finishing, building protection, cosmetic formulations or the treatment of surfaces. In most applications in these areas, it is important to use amine oils which have a high quality. The corresponding quality features include a) a residual volatility which is constant and as low as possible (e.g. due to short-chain alcohols, short-chain and/or cyclic siloxane components or amines), b) a constant viscosity, c) an optimum random distribution of the aminoalkyl groups in the copolymer and, where possible and necessary, d) optical clarity (freedom from turbidity). Especially the quality features b) and c) can generally be achieved only by effective equilibration of the polymer mixture, if appropriate coupled to a condensation reaction, although different amounts of volatile compounds are obtained depending on the reaction conditions set.

Amine oils are generally prepared by condensation and/or equilibration reactions between linear or cyclic organopolysiloxanes and aminoalkyl-functionalized alkoxysilanes or the partial or complete hydrolysis products thereof, generally under the action of catalytic amounts of basic inorganic or organic compounds.

According to the prior art at present, amine oils are prepared in a so-called batch process, i.e. campaign-by-campaign in batchwise processes in stirrers. Stirrers are very flexible owing to the variety of chemical reactions which can be carried out in them but—compared with continuous processes—are uneconomical in the case of very large production campaigns and high mass throughputs. This is due in particular to the fact that they can be automated only to a certain degree and that it is necessary to accept long times for heating up and cooling down, and for filling and emptying containers having a capacity of several cubic meters, thus entailing high operating costs and high labor costs. In addition, it is necessary to accept holding times of the reaction product, during which, for example, quality testing of the product is carried out. In particular, however, there are inevitably variations in the product composition and product quality from different production campaigns, with the result that product specifications have to be more widely formulated and high qualities are more difficult to achieve. Not least, a stirrer occupies substantially more space compared with a continuously operated plant and its throughput can be increased only through very great technical complexity or not at all (upscaling, debottlenecking).

One difficulty of current amine oil syntheses is the deactivation of the condensation or equilibration catalyst. If the basic catalyst is neutralized in a conventional manner with an acid, as described, for example, in U.S. Pat. No. 5,077,421, turbidity occurs as result of salt precipitates. However, continuous or semicontinuous filtration of a continuously produced amine oil is not desired since this gives rise to technical difficulties (e.g. change of filter in continuous operation), and the space-time yield decreases.

One possibility for avoiding such turbidity is the method of deactivating the tetraalkylammonium hydroxides or ammonium phosphates and borates used by thermal decomposition after the end of the reaction, as described, for example, in U.S. Pat. No. 4,652,662 (corresponding DE A 3418358). The resulting decomposition products must, however, be removed by distillation in vacuo. It is known to those skilled in the art that vacuum distillation takes several hours, is also energy-consumptive, and owing to the necessary residence time, cannot readily be carried out continuously. Finally, owing to traces of volatile organic amines, the process generally leads to an annoying and unacceptable odor during the use of the amine oils thusly prepared.

U.S. Pat. No. 7,129,369 (corresponding EP-A 1580215) describes a process in which, in spite of the use of alkali metal hydroxides and alcoholates, turbidity-free amine oils are obtained without a filtration step by neutralization with silyl phosphates, with the result that silicone-soluble neutralization products are obtained.

U.S. Pat. No. 4,128,568 (corresponding DE-A 2705563) describes a continuous process for the preparation of unfunctionalized organopolysiloxanes. The alkali metal hydroxides used must be deactivated by addition of trimethylchlorosilane. The organopolysiloxanes thus obtained must therefore be subjected to a downstream filtration and distillation step in order to remove the volatile disiloxanes produced by deactivation and thus to achieve the desired low residual volatility.

EP-A 1723193 describes a catalyst-free continuous process for the preparation of siloxanes having terminal aminoalkyl functions from siloxanes carrying terminal SiOH groups and cyclic silazanes. However, with cyclic silazanes, the process starts from a special and complicated amine precursor, inter alia with the aim of keeping the amine oil obtained free of volatile alcohols resulting from condensation reactions. In addition, siloxanes which carry on-chain SiOH groups which are required to produce amine oils having side groups by this process are not easily and directly accessible.

Continuous processes, as described, for example, in U.S. Pat. No. 3,853,934, in which the organopolysiloxane building blocks to be condensed are passed over an acidic silicate fixed-bed catalyst are not suitable for the preparation of amine oils since the amine groups spontaneously form salts with the acid groups and would deactivate the catalyst.

EP-A 0982347 describes a continuous process for the preparation of silicone polymers from siloxanes carrying SiOH groups or cyclic siloxane by means of catalytic amounts of basic phosphazenes. Apart from terminal group functionalization with various SiC-bonded hydrocarbon radicals, however, no heteroatom-substituted organically functionalized copolymers, such as, for example, amine oils, are described.

A very special continuous reactor for the preparation of siloxane polymers from siloxane mono- and oligomers is described in EP-A 0522776. There, the reaction mixture is foamed and passes through a porous wall into the reaction space. As a result of the large interface produced between the reaction mixture and gas space, volatiles can be readily removed from low-viscosity media. However, the process described is limited to condensation reactions of monomers or low-viscosity oligomers, and express equilibration of the polymers produced or the preparation of highly viscous silicone oils is not described. Moreover, a conventional neutralization of the catalysts is described, which generally leads to turbid products owing to salt formation.

Common to all processes described above is that the amine oils produced thereby cannot simultaneously exhibit satisfactory, and in particular, constant properties with respect to the principal quality features of residual volatility, quality of equilibration and, if appropriate, freedom from turbidity and constancy thereof. Downstream filtration or devolatilization steps or subsequent processing by equilibration would be necessary.

SUMMARY OF THE INVENTION

It was an object of the invention to provide a process in which the abovementioned disadvantages are avoided and in which organopolysiloxanes having aminoalkyl groups are obtained with constant product properties, in particular with low and consistent residual volatility, consistent desired viscosity and consistent random distribution of the siloxane units having aminoalkyl groups in the polymer, which requires avoidance of block structures of these units due to high quality equilibration. These and other objects are achieved by the invention, in which aminoalkylsilanes having 2 or 3 hydrolyzable groups are reacted in a continuous process with linear, branched, or cyclic organopolysiloxanes in a reaction space whose ratio of length to diameter is at least 4:1.

DETAILED DESCRIPTION OF THE PREFERRED EMBODIMENT(S)

Figure 1:
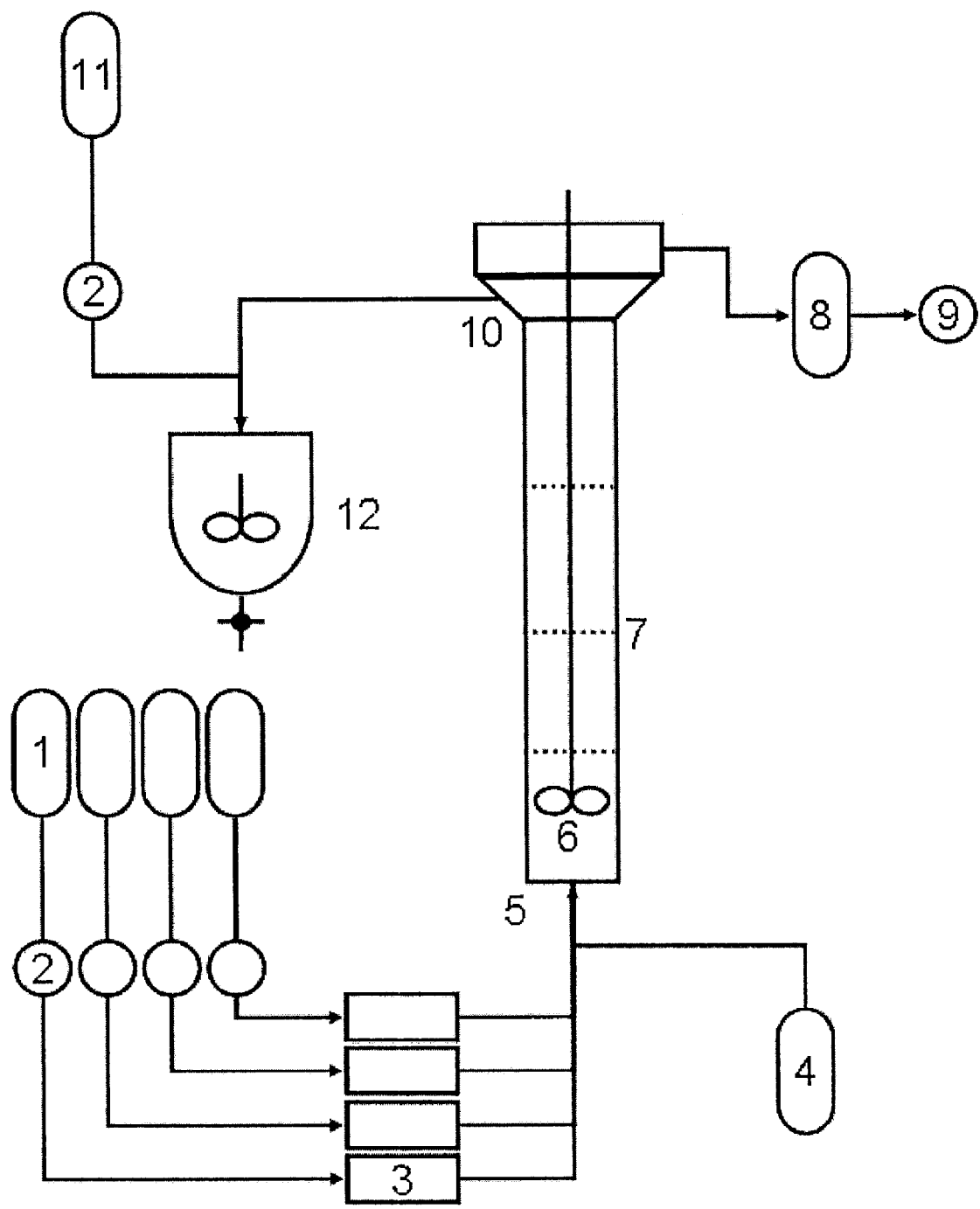
FIG. 1 illustrates schematically one embodiment of a continuous process in accordance with the invention.

The invention thus relates to a process for the preparation of organopolysiloxanes having aminoalkyl groups by
(i) reacting
  (A) linear, cyclic or branched organopolysiloxanes with
  (B) aminoalkylsilanes which have an SiC-bonded, basic nitrogen-containing hydrocarbon radical and 2 or 3 hydrolyzable groups,
    or the partial or complete hydrolysis products thereof,
  optionally in the presence of
  (C) basic catalysts
  and, optionally,
  (D) chain-terminating reagents and
(ii) optionally, after the reaction (i) neutralizing optionally used basic catalysts (C),
with the proviso that compounds (A), (B) and, when used, (D) are reacted, optionally in the presence of catalyst (C), continuously in a reaction space whose ratio of length to diameter is equal to or greater than four.

In the process of the invention, the compounds (A), (B), if appropriate (C) and if appropriate (D), are preferably passed continuously through the reaction space and (A), (B) and (D) are reacted there, the organopolysiloxanes having aminoalkyl groups which are thus obtained being removed continuously from the reaction space.

The reaction (i) is preferably effected in the presence of basic catalysts (c), and after the reaction (i), the neutralization of the basic catalysts (C) is preferably effected continuously.

Preferably, the reaction space has a ratio of length to diameter of from 4 to 1000, more preferably from 5 to 100, and most preferably from 6 to 10.

In the context of the present invention, the term organopolysiloxanes is intended to comprise both dimeric and oligomeric as well as polymeric siloxanes.

Amine oils having any desired possible amine number can be produced by the process of the invention. The amine number corresponds to the number of ml of a 1M HCl which are required for neutralizing 1 g of substance, and is given in millimoles of amine groups per gram of substance. Preferably, the amine number ranges from 0.001 to 12.5, preferably from 0.01 to 5, and most preferably from 0.1 to 3 mmol of amino groups per gram of substance.

The viscosities of the amine oils prepared by the inventive process may be from the viscosity of water to a firm consistency. The viscosity, always measured at 25° C., is preferably from 1 mPa·s to 10,000,000 mPa·s, more preferably from 100 mPa·s to 100,000 mPa·s, and most preferably from 500 mPa·s to 50,000 mPa·s.

For carrying out the process of the invention, the starting compounds (A), (B) and if appropriate (D) are passed through a chamber whose length/diameter ratio is equal to or greater than four. Such a chamber may be present, for example, in loop reactors, kneaders, extruders, flow tubes, tubular reactors, microreactors or centrifugal pumps, and in any desired combinations thereof. Experience has shown that the procedure in an extruder or kneader is suitable in particular for the production of highly viscous or firm amine oils (viscosity measured at 25° C. greater than 50,000 mPa·s), and the procedure in a tubular reactor is suitable in particular for producing flowable amine oils (viscosity measured at 25° C. less than 50,000 mPa·s). The procedure in an extruder or kneader for producing highly viscous or firm amine oils (viscosity measured at 25° C. greater than 50,000 mPa·s) is therefore preferred, and the procedure in a tubular reactor for the production of flowable amine oils (viscosity measured at 25° C. less than 50,000 mPa·s) is particularly preferred.

In the process of the invention, the starting materials and, if appropriate, the catalyst are preferably transported or pumped continuously into the reaction space and mixed therein, it being possible to preheat the starting materials and, if appropriate, the catalyst before reaching the reaction space or before combination in the reaction space. Inter alia, electrical heating jackets and heating wires which surround the starting material feed lines and either double-walled starting material feed lines through which a heated medium flows or single-walled starting material feed lines which run through the bath of a heated medium are suitable for the preheating. If the catalyst is not introduced into the reaction space with the starting materials, it may be a basic catalyst immobilized in the reaction space or applied to an optionally polymeric support. The individual volume flows of the starting materials among one another are appropriately regulated in order to obtain the desired random distribution of functional groups in the polymer and the desired product molecular weight distribution. The total volume flow in the entire reactor depends on the desired residence time in the reactor. The reaction space can be heated and can be thoroughly mixed or kneaded as a whole or only partly. Inter alia, electrical heating jackets and heating wires which surround the reaction space or a double-walled reaction space through which a heated medium flows are suitable for heating. Inter alia, so-called static mixers, which can be mounted in the reaction space, or mechanically driven stirrers (driven directly, for example via a shaft, or a combination of magnetic clutch and shaft) or gas streams (e.g. nitrogen) which cause turbulence are suitable for the thorough mixing. The material of the reactor may vary from metal, such as chromium-vanadium steel reactors, or enamel steel reactors, to glass reactors.

The reactions in the reaction space are preferably effected at a temperature of from 50 to 180° C., more preferably from 80 to 130° C. The reaction times and hence the average residence times are preferably from 1 to 180 minutes, preferably from 10 to 120 minutes and most preferably from 20 to 90 minutes. In addition, the pressure in the reaction space can be regulated to any desired value adapted to the respective reactor type, values from the atmospheric pressure surrounding the reactor (about 1013 mbar) to 0.1 mbar being preferred, values from 100 to 1 mbar being particularly preferred, for continuously removing any volatile components occurring during the reaction via the gas phase by distillation. For promoting the removal of volatile components by distillation, a so-called purge gas stream can additionally be passed through the reaction space, inert nitrogen gas being preferred.

After the end of the reaction, i.e. after passing through the reaction zone in the desired residence time, any catalyst (C) present in the reaction mixture is deactivated. This can be effected, for example, by chemical reaction of the catalyst with a deactivator—generally a neutralizing agent or inhibitor—or by thermal deactivation by the reaction mixture passing through a reactor zone brought specially to the temperature required for this purpose. If solids are present in the transported reaction product owing to the reaction procedure or the catalyst deactivation, they can be removed, if appropriate, by downstream processes. Such downstream processes may be a continuous filtration or a continuous extraction with a suitable solvent or a continuous adsorptive process over a suitable adsorbent.

After passing through a cooling zone in which the reaction product is cooled to a desired temperature by heat exchange, the reaction product can be continuously filled into storage containers or end containers or continuously fed to further plant components, for example, a continuous dispersing apparatus for the preparation of dispersions containing the amine oils obtained by the process.

In a preferred embodiment of the process according to the invention (numbers in brackets relate to FIG. 1), the starting compounds (A), (B) and, if appropriate, (D) and the catalyst (C) are passed from corresponding containers (1) via pumps or pump/balance combinations (2) continuously through preheater (3) and then through a heatable reactor (5). If appropriate, a purge gas stream for removing low boilers can be connected through a nitrogen feed line (4). One or more stirrers or static mixing elements (6) and one or more perforated trays or sieve trays (7) are present in the reactor. Low boilers can be condensed in a cold trap (8) with the aid of a regulated vacuum pump (9). After flowing through the product transfer line (10), the catalyst deactivator is metered in continuously from the deactivator container (11) and the product is collected and cooled in a stirred product collection tank (12).

In the process of the invention, the organopolysiloxanes (A) include linear polydiorganosiloxanes of the general formula

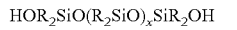 (I) and

 (II)

cyclic polydiorganosiloxanes of the general formula

 (III)

and mixtures thereof,
in which R may be identical or different and is a monovalent optionally halogenated hydrocarbon radical having 1 to 18 carbon atoms,
x is 0 or an integer from 1 to 800, preferably 10 to 450, and most preferably 30 to 150,
y is 0 or an integer from 1 to 800, preferably 10 to 450, and most preferably 30 to 150, and
z is an integer from 3 to 12.

In addition to diorganosiloxane units $R_2SiO$, other siloxane units may be present within or along the siloxane chain of the siloxanes of the above-mentioned formulae (I) (III), which is not usually shown by such formulae. Examples of such other siloxane units, generally present only as impurities, are those of the formulae $RSiO_{3/2}$, $R_3SiO_{1/2}$ and $SiO_2$, in which R has the meaning stated previously. In the process, the organopolysiloxanes (A) are preferably used in amounts of 99.99 to 0.1% by weight, more preferably 99.9 to 18% by weight, and most preferably 99 to 51% by weight, based in each case on the total weight of the reaction mixture of (A), (B), (C), and if appropriate, (D).

The aminoalkylsilanes (B) are preferably those of the general formula

 (IV)

and partial or complete hydrolysis products thereof,
in which
R has the meaning stated above therefor,
X is a hydrolyzable group selected from the group consisting of $OR^1$, $NR'_2$ and —Cl, preferably $OR^1$,
$R^1$ is a monovalent alkyl radical having 1 to 18 carbon atoms, which may be substituted by one or two ether oxygen atoms,
R' is hydrogen or a monovalent hydrocarbon radical having 1 to 18 carbon atoms,
Z is a monovalent SiC-bonded basic nitrogen-containing hydrocarbon radical and n is 2 or 3.

Examples of hydrocarbons R, $R^1$ or R' are alkyl radicals such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radicals such as n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radicals, decyl radicals such as the n-decyl radical, dodecyl radicals such as the n-dodecyl radical, and octadecyl radicals such as the n-octadecyl radical; cycloalkyl radicals such as cyclopentyl, cyclohexyl, cycloheptyl and methylcyclohexyl radicals; aryl radicals such as the phenyl, naphthyl, anthryl and phenanthryl radicals; alkaryl radicals, such as the o-, m- and p-tolyl radicals, xylyl radicals and ethylphenyl radicals; and aralkyl radicals such as the benzyl radical and the α- and the β-phenylethyl radicals.

The hydrocarbon radicals R, $R^1$ or R' optionally contain an aliphatic double bond. Examples are alkenyl radicals, such as the vinyl, allyl, 5-hexen-1-yl, E-4-hexen-1-yl, Z-4-hexen-1-yl, 2-(3-cyclohexenyl)ethyl and cyclododeca-4,8-dienyl radical. Preferred radicals R having an aliphatic double bond are the vinyl, allyl and 5-hexen-1-yl radical. Preferably, however, not more than 1% of the hydrocarbon radicals R contain a double bond.

Examples of halogenated radicals R are haloalkyl radicals, such as the 3,3,3-trifluoro-n-propyl radical, the 2,2,2,2',2',2'-hexafluoroisopropyl radical, and the heptafluoroisopropyl radical, and haloaryl radicals, such as the o-, m- and p-chlorophenyl radical.

The radical R is preferably a monovalent hydrocarbon radical having 1 to 18 carbon atoms, the methyl radical being particularly preferred.

Examples of $R^1$ are $CH_3$—, $CH_3CH_2$—, $(CH_3)_2CH$—, $CH_3CH_2CH_2$—, $CH_3CH_2CH_2CH_2$—, $CH_3CH_2OCH_2CH_2$—, $CH_3CH_2OCH_2$— and $CH_3OCH_2CH_2$— radicals.

Preferably, Z in formula (IV) is a radical of the formula $$-R^2[NR^3-R^4-]_g NR^3{}_2$$

in which $R^2$ is a divalent linear or branched hydrocarbon radical having 1 to 18 carbon atoms,
$R^3$ has the meaning of $R^1$ or is an acyl radical, preferably a hydrogen atom,
$R^4$ is a divalent hydrocarbon radical having 1 to 6 carbon atoms and
g is 0, 1, 2, 3 or 4, preferably 0 or 1.

Preferred examples of radicals Z are:
$H_2N(CH_2)_3—$,
$H_2N(CH_2)_2NH(CH_2)_3—$,
$H_2N(CH_2)_2NH(CH_2)CH(CH_3)CH_2—$,
(cyclohexyl)$NH(CH_2)_3—$,
$CH_3NH(CH_2)_3—$,
$(CH_3)_2N(CH_2)_3—$,
$CH_3CH_2NH(CH_2)_3—$,
$(CH_3CH_2)_2N(CH_2)_3—$,
$CH_3NH(CH_2)_2NH(CH_2)_3—$,
$(CH_3)_2N(CH_2)_2NH(CH_2)_3—$,
$CH_3CH_2NH(CH_2)_2NH(CH_2)_3—$,
$(CH_3CH_2)_2N(CH_2)_2NH(CH_2)_3—$,
and the partly and completely acylated forms thereof.

Examples of aminoalkylsilanes (IV) are
(3-aminopropyl)dimethoxymethylsilane,
(3-aminopropyl)diethoxymethylsilane,
(3-aminopropyl)trimethoxysilane,
(3-aminopropyl)triethoxysilane,
[N-(2-aminoethyl)-3-aminopropyl]dimethoxymethylsilane,
[N-(2-aminoethyl)-3-aminopropyl]diethoxymethylsilane,
[N-(2-aminoethyl)-3-aminopropyl]trimethoxysilane,
[N-(2-aminoethyl)-3-aminopropyl]triethoxysilane,
(aminomethyl)dimethoxymethylsilane,
(aminomethyl)diethoxymethylsilane,
(aminomethyl)trimethoxysilane, and
(aminomethyl)triethoxysilane.

Particularly preferred are
[N-(2-aminoethyl)-3-aminopropyl]dimethoxymethylsilane,
[N-(2-aminoethyl)-3-aminopropyl]trimethoxysilane and
(3-aminopropyl)dimethoxymethylsilane,
and the cyclic and linear partial or complete hydrolysis products thereof.

The aminoalkylsilane hydrolysis products (B) are preferably prepared from aminoalkyl-functional dialkoxysilanes, such as (3-aminopropyl)dimethoxymethylsilane or [N-(2-aminoethyl)-3-aminopropyl]dimethoxymethylsilane, by hydrolysis in water.

Aminoalkylsilane hydrolysis products (B) used are therefore preferably those of the general formula $$HO(ZRSiO)_m H \qquad (VI)$$

in which R and Z have the meaning stated above therefor and m is an integer from 2 to 50.

Aminoalkylsilanes (B) or the partial or complete hydrolysis products thereof are preferably used in amounts of from 0.01 to 99.9%, preferably from 0.1 to 82% and most preferably from 1 to 49%, based in each case on the total weight of the polysiloxanes (A) and if appropriate, (D).

Condensation and equilibration catalysts can be used as basic catalysts (C) in the process according to the invention. Alkali metal or alkaline earth metal hydroxides, oxides, alcoholates or siloxanolates, which, if appropriate, are dissolved beforehand in a suitable solvent, are preferably used as basic catalysts (C). Alkali metal hydroxides, alkali metal alcoholates, alkali metal siloxanolates and mixtures thereof are preferably used as basic catalysts (C). Examples of alkali metal hydroxides are potassium hydroxide and sodium hydroxide. Examples of alkali metal alcoholates are sodium methanolate and sodium ethanolate. An example of an alkali metal siloxanolate is sodium siloxanolates.

Potassium or sodium hydroxide (if appropriate in methanol solvent or water) and sodium methanolate (if appropriate in methanol solvent) are preferably used.

The basic catalysts (C) are preferably used in amounts of from 1 to 1000 ppm by weight, more preferably from 10 to 400 ppm by weight, and most preferably from 30 to 200 ppm by weight, based in each case on the total weight of the reaction mixture of (A), (B), (C) and if appropriate (D).

If reactive Si OH-terminated polysiloxanes of the formula (I) are used in the process according to the invention, a chain-terminating reagent (D), a so-called "chain stopper," "stopper siloxane," or more simply, just "stopper" can additionally be used. In principle, all compounds which can react with Si—OH groups and are monofunctional with regard to their reactivity with Si—OH groups or can form such monofunctional groups are suitable for this purpose. In addition, these chain-terminating reagents may carry further functional groups which do not react with the Si—OH groups or the aminoalkyl groups and which can be reacted in an optional further reaction of the amine oil prepared by the process according to the invention, in order to achieve additional effects.

In the process according to the invention, chain-terminating reagents (D) selected from the group consisting of monoalkoxysilanes, aminomonoalkoxysilanes, linear and cyclic silazanes, alcohols, short-chain linear diorganopolysiloxanes and mixtures thereof are preferably used. These include, for example, monoalkoxytrialkylsilanes, (aminoalkyl)monoalkoxydialkylsilanes, linear or cyclic silazanes, alcohols, short-chain linear polydiorganosiloxanes or mixtures thereof.

Examples of monoalkoxytrialkylsilanes are those of the formula $$R_3Si(OR^1) \qquad (VII), and$$

examples of (aminoalkyl)monoalkoxydialkylsilanes are those of the formula $$R_2ZSi(OR^1) \qquad (VIII)$$

in which R, $R^1$ and Z have the meaning stated above therefor.

Examples of alcohols are those of the general formula $$H—[O(CHR^5)_l]_k OR^6 \qquad (IX)$$

in which R has the meaning stated above therefor,
$R^5$ may be identical or different and is a hydrogen atom or a $C_1$- to $C_{18}$-hydrocarbon radical,
$R^6$ is a $C_1$- to $C_{30}$-hydrocarbon radical or a group of the general formula (C=O)$R^7$, in which $R^7$ is a radical $R^5$ or $O—R^5$,
l is 2, 3 or 4 and
k is 0 or an integer from 1 to 100.

Examples of short-chain linear polydiorganosiloxanes as chain-terminating reagent (D) are short-chain polydiorganosiloxanes which have terminal triorganosilyloxy groups and are of the formula $$R_3SiO(SiR_2O)_v SiR_3 \qquad (X), and$$

short-chain polydiorganosiloxanes which have hydroxy- or alkoxydiorganosilyloxy groups and are of the formula $$(R''O)R_2SiO(SiR_2O)_w SiR_3 \qquad (XI)$$

in which R has the meaning stated above therefor,
R" is a hydrogen atom or a radical $R^1$, v is 0 or an integer from 1 to 150, preferably from 30 to 100, and w is 0 or an integer from 1 to 150, preferably from 30 to 100.

If, in the process according to the invention, a stopper or stopper siloxane (D) is used as the chain-terminating reagent, this is preferably used in amounts of from 0.01 to 50%, more preferably from 0.05 to 30%, and most preferably from 1 to 20%, based in each case on the total weight of the reaction mixture of (A), (B), (C) and (D).

The deactivation of the basic catalyst (C) can be effected by the addition of neutralizing agents (E) which form salts with the basic catalysts. Such neutralizing agents may be, for example, carboxylic acids or mineral acids. Carboxylic acids, such as methanoic acid (formic acid), ethanoic acid (acetic acid) or propanoic acid are preferred.

The deactivation of the basic catalyst (C) is preferably effected, however, by the addition of neutralizing agents (E) which, with the basic catalysts, form salts which are soluble in the amine oils obtained and hence produce no turbidity at all. Examples of such neutralizing agents (E) are long-chain carboxylic acids which are liquid at room temperature, such as n-octanoic acid, 2-ethylhexanoic acid, n-nonanoic acid and oleic acid, hexadecanoic and octadecanoic acid, carbonic acid esters such as propylene carbonate, or carboxylic anhydrides such as octenylsuccinic anhydride.

Further examples of neutralizing agents (E) which, with the basic catalysts, form salts which are soluble in the amine oils obtained and hence produce no turbidity at all are triorganosilyl phosphates, preferably trimethylsilyl phosphates, and triorganophosphates, preferably mixtures of mono-, di- and triisotridecyl phosphates (obtainable under the name Hordaphos® MDIT from Clariant). Compositions substantially comprising 0-50% by weight of monosilyl phosphate of the formula:

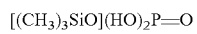

20-100% by weight of disilyl phosphate of the formula:

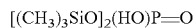

0-70% by weight of trisilyl phosphate of the formula:

the total amount being 100% by weight, are preferably used as trimethylsilyl phosphates. The amount of neutralizing agents (E) required depends on the amount of basic catalysts (C) used and is preferably from 0.05 to 0.50%, preferably from 0.15 to 0.30%, based in each case on the total weight of the reaction mixture of (A), (B), (C) and if appropriate (D). The neutralization can be effected before or after the cooling of the reaction mixture.

The organopolysiloxanes (amine oils) obtained by the process according to the invention and having aminoalkyl groups preferably have a residual volatility of less than 4% by weight, more preferably less than 2% by weight, and most preferably less than 1% by weight. The residual volatility is a thermally determined value and is defined as the amount of volatile constituents in % by weight on heating a sample amount of 5 g at 120° C. for a time of 60 min (120° C./5 g/60 min). A major part of the volatile constituents are cyclic siloxanes, octamethyltetrasiloxane (D4) being present in addition to higher cycles.

A particularly preferred embodiment of the process according to the invention gives amine oils having extremely low residual volatilities, preferably less than 2%, more preferably less than 1% by weight, in particularly short average residence times, preferably from 1 to 50 minutes, without it being necessary to apply to the reactor a reduced pressure relative to the atmospheric pressure surrounding the reactor. In this particularly preferred embodiment of the process of the invention, partial and complete hydrolysis products of the aminoalkylsilanes (B), preferably aminoalkylsilane hydrolysis products of the formula (VI), are used as aminoalkylsilanes (B). In this process, organopolysiloxanes (A) of the formulae (I) and/or (II) are preferably used together with the aminoalkylsilane hydrolysis products (B), preferably of the formula (VI).

The inventive process has the advantage that organopolysiloxanes having aminoalkyl groups (amine oils) having constant product quality, in particular a low and consistent residual volatility, a consistent desired viscosity and a good and consistent equilibration quality (avoidance of block structures of the aminoalkyl groups in the organopolysiloxanes having aminoalkyl groups) are obtained. By using suitable neutralizing agents (E), it is possible, if desired, to obtain in particular, turbidity-free amine oils.

Organopolysiloxanes which have aminoalkyl groups and are of the general formula

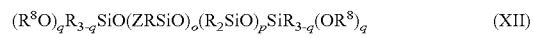 (XII)

in which R and Z have the meaning stated above therefor, $R^8$ is a hydrogen atom or $R^1$, o is an integer from 1 to 1000, preferably from 2 to 260, p is an integer from 0 to 2500, preferably from 50 to 650, and q is 0 or 1, are preferably obtained by the process according to the invention.

The organopolysiloxanes having aminoalkyl groups obtained by the process can be used, inter alia, as compositions for the treatment of porous or nonporous, absorptive or nonabsorptive substrates, such as leather, webs, cellulosic materials (pulp and paper), textiles, nonwovens and tissues, natural and manmade fibers, glasses and ceramics, porous mineral building materials, construction coatings and wood, and as a constituent of polishes and coating materials for, for example, coated and uncoated metals, plastics and laminates, mainly properties such as water repellency and/or a soft handle being imparted to the substrates described by the treatment with the organopolysiloxanes carrying aminoalkyl groups. Furthermore, the organopolysiloxanes having aminoalkyl groups obtained by the process can be used, inter alia, as a constituent of antifoam formulations, for paper sizing and the coating of gypsum plasterboard, as care compositions for coated and uncoated metals, plastics, laminates, vulcanized and unvulcanized rubbers, as dispersants, as wetting agents, as release agents or auxiliaries, as paint additives, as PU foam stabilizers and, in the area of personal hygiene, as active ingredients in hair conditioners, hair shampoos and skincare compositions. The organopolysiloxanes carrying aminoalkyl groups, when dissolved in organic solvents or dispersed in water, are preferably used in the form of aqueous emulsions. The organopolysiloxanes having aminoalkyl groups can be used in the free amine form or in salt form, for example as an ammonium chloride salt or ammonium carboxylate salt, by addition of hydrochloric acid or the corresponding carboxylic acid. Compositions which contain the organopolysiloxanes having aminoalkyl groups may contain further ingredients, such as surfactants, thickeners, rheology-modifying additives, perfumes, waxes, plasticizers, cleaning agents, lubricating oils, electrolytes, flavors, biocides or pharmaceutical or cosmetic active ingredients.

Selected examples which are intended to illustrate the invention follow.

The invention itself is, however, by no means limited to these examples. The percentages used in the examples in the determination of the residual volatilities (120° C./5 g/60 min) are based on weight.

All viscosities stated were measured at 25° C.

For Examples 1-6, a tubular glass reactor (internal diameter 80 mm, height 500 mm, length/diameter ratio=6.25, volume about 2.5 l) was used as the continuous reactor. The reactor was divided into a plurality of zones separated by perforated PTFE trays and was equipped with a stirrer. The starting materials and the catalyst (regarding reaction parameters and ratios, cf. following tables of the respective examples) were heated to the stated temperatures by passage through thermostating units and were transported in the stated ratios continuously via pump systems into the reaction zone set at reactor temperature and reactor pressure.

The termination of the reaction was achieved by continuously metering in a deactivator at a fixed position in the tubular reactor. This position was in the region of the product discharge after leaving the heated reaction zone. This gives the average residence time of the reaction mixture in the reaction zone, which is established by the total throughput of starting materials transported. From the reactor volume of about 2.5 l, for example, an average residence time of 1 h is obtained with a throughput of 2.5 l/h, and an average residence time of 2 h with a throughput of 1.25 l.

The product emerged into a cooled and stirred collecting container in order to distribute the deactivator uniformly in the product and to cool the product.

Comparative Experiment 1 (Batchwise):

For the preparation of a turbidity-free amine oil having an amine number of 0.25 and a viscosity of 200-220 mPa·s, the following starting materials according to Table 1a and b were used:

TABLE 1a

| Polydimethylsiloxane | HO—SiMe$_2$—(O—SiMe$_2$)$_{40}$—OH |
| --- | --- |
| (Aminoalkyl)silane | [N-(2-Aminoethyl)-3-aminopropyl] dimethoxymethylsilane |
| Stopper siloxane | Me$_3$Si—(O—SiMe$_2$)$_{23}$—OSiMe$_3$ |
| Catalyst | Sodium methanolate in methanol (30% by weight) |
| Deactivator | Tris(trimethylsilyl) phosphate |

TABLE 1b

|  | Amount used | % by weight | % by volume |
| --- | --- | --- | --- |
| Polydimethylsiloxane | 872 G | 80.73 | 80.83 |
| (Aminoalkyl)silane | 26.5 G | 2.45 | 2.31 |
| Stopper siloxane | 179 g | 16.57 | 16.59 |
| Catalyst | 0.67 g | 0.06 | 0.08 |
| Deactivator | 0.6 g | 0.19 | 0.18 |

A mixture of 872 g of polydimethylsiloxane, 26.5 g of (aminoalkyl)silane, 179 g of stopper siloxane and 0.67 g of catalyst solution was heated to 80° C. with stirring at a pressure reduced to 50 mbar in a 2 l three-necked flask (length/diameter ratio=1) having a mechanical stirrer, internal thermometer and reflux condenser. The volatile components were collected in a cold trap cooled with liquid nitrogen. After 90 min, the plant was brought to atmospheric pressure by means of a nitrogen stream, the deactivator was added and cooling was effected with stirring.

A colorless turbidity-free amine oil was obtained.

Table 1c below summarizes the analytical data of tests carried out independently of one another according to the preceding method, the same batches of starting materials having been used.

TABLE 1c

|  | Test | | | | Standard |
| --- | --- | --- | --- | --- | --- |
|  | 1 | 2 | 3 | 4 | deviation |
| Residual volatility of the product [%] | 4.6 | 5.3 | 5.4 | 4.3 | 0.46 |
| Viscosity [mPa · s] | 238 | 183 | 155 | 220 | 32.2 |

EXAMPLE 1

In contrast to comparative experiment 1, a reaction mixture having the same starting material volume distribution according to Table 2a was passed with the following reaction parameters through the above-described tubular reactor according to the invention: the product discharge and the continuous catalyst deactivation were effected after an average residence time of 90 min. After a reactor run time of 10 h, the plant was brought to room pressure and the product collecting container was emptied. A colorless turbidity-free oil was obtained.

TABLE 2a

| Proportion of polydimethylsiloxane transported | 80.83% by vol. |
| --- | --- |
| Proportion of (aminoalkyl)silane transported | 2.31% by vol. |
| Proportion of stopper transported | 16.59% by vol. |
| Proportion of catalyst transported | 0.08% by vol. |
| Proportion of deactivator transported | 0.18% by vol. |
| Internal reactor temperature | 80° C. |
| Temperature of thermostating unit for polydimethylsiloxane and (aminoalkyl)silane | 80° C. |
| Temperature of thermostating unit for stopper | 50° C. |
| Reactor pressure | 50 mbar |

During the reactor run time, samples of the reaction product were taken. Table 2b below summarizes the analytical data of the samples, the same batches of starting materials having been used as in comparative experiment 1.

TABLE 2b

|  | Sample | | | | | | Standard |
| --- | --- | --- | --- | --- | --- | --- | --- |
|  | 1 | 2 | 3 | 4 | 5 | 6 | deviation |
| Residual volatility of the product [%] | 3.5 | 3.3 | 3.4 | 3.3 | 3.5 | 3.4 | 0.08 |
| Viscosity [mPa · s] | 210 | 228 | 219 | 224 | 221 | 224 | 5.7 |

High-resolution $^{29}$Si-NMR investigations of samples 1 6 disclosed an excellent equilibration quality. Block structures of the [N-(2-aminoethyl)-3-aminopropyl]methylsilyloxy units were not observed. The comparison of the standard deviations of the residual volatilities and viscosities obtained under comparative experiment 1 and example 1 illustrates the more constant product quality of the amine oils obtained by the process according to the invention (Example 1). The absolute residual volatilities of the amine oils obtained are moreover lower after the process according to the invention (Example 1), which additionally contributes to an increased product quality.

Comparative EXAMPLE 2

Length/Diameter Ratio=1.56

The experiment under Example 1 was repeated but the tubular reactor used was shortened from the length 500 mm (length/diameter ratio=6.25) to the length 125 mm (length/diameter ratio=1.56) at the same diameter. The residence time was 90 min.

During the reactor run time, samples of the reaction product were taken. Table 3a below summarizes the analytical data of the samples, the same batches of starting materials having been used as in Example 1.

TABLE 3A

| | Sample | | | | | | Standard |
|---|---|---|---|---|---|---|---|
| | 1 | 2 | 3 | 4 | 5 | 6 | deviation |
| Residual volatility of the product [%] | 5.2 | 4.7 | 5.0 | 4.2 | 5.5 | 4.9 | 0.41 |
| Viscosity [mPa·s] | 94 | 104 | 125 | 116 | 93 | 96 | 12.0 |

The viscosities obtained for samples 1-6 were significantly too low and showed that the desired product was not obtained. The residual volatilities of the samples were substantially increased and varied more greatly than under Example 1. In addition, subsequent turbidity occurred in all samples. High-resolution $^{29}$Si NMR investigations showed inadequate equilibration quality of all samples.

EXAMPLE 2

The following starting materials according to Table 4a were used.

TABLE 4a

| | |
|---|---|
| Polydimethylsiloxane of the type | HO—SiMe$_2$—(O—SiMe$_2$)$_{40}$—OH |
| (Aminoalkyl)silane | [N-(2-Aminoethyl)-3-aminopropyl]dimethoxymethylsilane |
| Stopper | n-Hexyl glycol |
| Catalyst | Sodium methanolate in methanol (30% by weight) |
| Deactivator | Tris(trimethylsilyl) phosphate |

The product discharge and the continuous catalyst deactivation were effected after an average residence time of 90 min. After a reactor run time of 6 h, the plant was brought to room pressure and the product collecting container was emptied. A colorless turbidity-free oil having a viscosity of 1450 mPa·s, a volatility (120° C./5 g/60 min) of 1.09% by weight and an amine number of 0.27 was obtained. High-resolution $^{29}$Si NMR investigations disclosed no block structures of the [N-(2-aminoethyl)-3-aminopropyl]methylsilyloxy units.

The amounts of starting materials and process parameters are summarized in Table 4b.

TABLE 4b

| | |
|---|---|
| Proportion of polydimethylsiloxane transported | 95.0% by vol. |
| Proportion of (aminoalkyl)silane transported | 2.7% by vol. |
| Proportion of stopper transported | 2.0% by vol. |
| Proportion of catalyst transported | 0.1% by vol. |
| Proportion of deactivator transported | 0.2% by vol. |
| Internal reaction temperature | 85° C. |

TABLE 4b-continued

| | |
|---|---|
| Temperature of thermostating unit for polydimethylsiloxane and (aminoalkyl)silane | 85° C. |
| Temperature of thermostating unit for stopper | 50° C. |
| Reactor pressure | 50 mbar |

EXAMPLE 3

The following starting materials according to Table 5a were used.

TABLE 5a

| | |
|---|---|
| Polydimethylsiloxane of the type | HO—SiMe$_2$-(O—SiMe$_2$)$_{40}$-OH |
| (Aminoalkyl)silane | [N-(2-Aminoethyl)-3-aminopropyl]dimethoxymethylsilane |
| Catalyst | Sodium methanolate in methanol (30% by weight) |
| Deactivator | Hordaphos ® MDIT |

The product discharge and the continuous catalyst deactivation were effected after an average residence time of 90 min. After a reactor run time of 6 h, the plant was brought to room pressure and the product collecting container was emptied. A colorless turbidity-free oil having a viscosity of 1250 mPa·s, a volatility (120° C./5 g/60 min) of 0.53% by weight and an amine number of 0.30 was obtained. High-resolution $^{29}$Si NMR investigations disclosed no block structures of the [N-(2-aminoethyl)-3-aminopropyl]methylsilyloxy units.

The amounts of starting materials and process parameters are summarized in Table 5b.

TABLE 5b

| | |
|---|---|
| Proportion of polydimethylsiloxane transported | 97.1% by vol. |
| Proportion of (aminoalkyl)silane transported | 2.9% by vol. |
| Proportion of catalyst transported | 0.02% by vol. |
| Proportion of deactivator transported | 0.03% by vol. |
| Internal reaction temperature | 80° C. |
| Temperature of thermostating unit for polydimethylsiloxane and (aminoalkyl)silane | 80° C. |
| Reactor pressure | 250 mbar |

EXAMPLE 4

The following starting materials according to Table 6a were used.

TABLE 6a

| | |
|---|---|
| Polydimethylsiloxane of the type | HO—SiMe$_2$-(O-SiMe$_2$)$_{24}$5-OH |
| (Aminoalkyl)silane hydrolysis product | (3-Aminopropyl)dimethoxymethylsilane hydrolysis product |
| Catalyst | Potassium hydroxide in ethanol(20% by weight) |
| Deactivator | Acetic acid |

The product discharge and the continuous catalyst deactivation were effected after an average residence time of 10 min. After a reactor run time of 6 h, the plant was brought to room pressure and the product collecting container was emptied. A colorless oil having a viscosity of 6700 mPa·s (25° C.), a volatility (120° C./5 g/60 min) of 0.21% by weight and an amine number of 0.16 was obtained. High-resolution $^{29}$Si NMR investigations disclosed no block structures of the (aminopropyl)methylsilyloxy units.

The amounts of starting materials and process parameters are summarized in Table 6b.

TABLE 6b

| | |
|---|---|
| Proportion of polydimethylsiloxane transported | 98.1% by vol. |
| Proportion of (aminoalkyl)silane hydrolysis product transported | 1.8% by vol. |
| Proportion of catalyst transported | 0.1% by vol. |
| Proportion of deactivator transported | 0.01% by vol. |
| Internal reaction temperature | 100° C. |
| Temperature of thermostating unit for polydimethylsiloxane and (aminoalkyl)silane hydrolysis product | 100° C. |
| Reactor pressure | no vacuum |

EXAMPLE 5

The following starting materials according to Table 7a were used.

TABLE 7a

| | |
|---|---|
| Polydimethylsiloxane of the type | Me$_3$Si—(O—SiMe$_2$)$_{310}$-OSiMe$_3$ |
| (Aminoalkyl)silane hydrolysis product | (3-Aminopropyl)dimethoxymethylsilane hydrolysis product |
| Catalyst | Potassium hydroxide in ethanol(20% by weight) |
| Decactivator | Acetic acid |

The product discharge and the continuous catalyst deactivation were effected after an average residence time of 10 min. After a reactor run time of 6 h, the plant was brought to room pressure and the product collecting container was emptied. A colorless oil having a viscosity of 1100 mPa·s (25° C.), a volatility (120° C./5 g/60 min) of 0.62% by weight and an amine number of 0.25 was obtained. High-resolution $^{29}$Si NMR investigations disclosed no block structures of the (aminopropyl)methylsilyloxy units.

The amounts of starting materials and process parameters are summarized in Table 7b.

TABLE 7b

| | |
|---|---|
| Proportion of polydimethylsiloxane transported | 97.6% by vol. |
| Proportion of (aminoalkyl)silane hydrolysis product transported | 2.3% by vol. |
| Proportion of catalyst transported | 0.1% by vol. |
| Proportion of deactivator transported | 0.01% by vol. |
| Internal reaction temperature | 100° C. |
| Temperature of thermostating unit for polydimethylsiloxane and (aminoalkyl)silane hydrolysis product | 100° C. |
| Reactor pressure | no vacuum |

EXAMPLE 6

The following starting materials according to Table 8a were used.

TABLE 8a

| | |
|---|---|
| Polydimethylsiloxane of the type | HO—SiMe$_2$-(O—SiMe$_2$)$_{245}$-OH |
| (Aminoalkyl)silane hydrolysis product | (3-Aminopropyl)dimethoxymethylsilane hydrolysis product |
| Catalyst | Sodium methanolate in methanol(30% by weight) |
| Deactivator | Acetic acid |

The product discharge and the continuous catalyst deactivation were effected after an average residence time of 25 min. After a reactor run time of 6 h, the plant was brought to room pressure and the product collecting container was emptied. A colorless oil having a viscosity of 13,300 mPa·s (25° C.), a volatility (120° C./5 g/60 min) of 0.20% by weight and an amine number of 0.10 was obtained. High-resolution $^{29}$Si NMR investigations disclosed no block structures of the (aminopropyl)methylsilyloxy units.

The amounts of starting materials and process parameters are summarized in Table 8b.

TABLE 8b

| | |
|---|---|
| Proportion of polydimethylsiloxane transported | 98.8% by vol. |
| Proportion of (aminoalkyl)silane hydrolysis product transported | 1.2% by vol. |
| Proportion of catalyst transported | 0.02% by vol. |
| Proportion of deactivator transported | 0.01% by vol. |
| Internal reaction temperature | 80° C. |
| Temperature of thermostating unit for polydimethylsiloxane and (aminoalkyl)silane hydrolysis product | 80° C. |
| Reactor pressure | no vacuum |

EXAMPLE 7

The following starting materials according to Table 9a were used.

TABLE 9a

| | |
|---|---|
| Polydimethylsiloxane of the type | HO—SiMe$_2$-(O—SiMe$_2$)$_{40}$-OH |
| (Aminoalkyl)silane hydrolysis product | (3-Aminopropyl)dimethoxymethylsilane hydrolysis product |
| Stopper | Me$_3$Si—(O—SiMe$_2$)$_{140}$-OSiMe$_3$ |
| Catalyst | Sodium methanolate in methanol(30% by weight) |
| Deactivator | Tris(trimethylsilyl) phosphate |

The product discharge and the continuous catalyst deactivation were effected after an average residence time of 120 min. After a reactor run time of 6 h, the plant was brought to room pressure and the product collecting container was emptied. A colorless turbidity-free oil having a dynamic viscosity of 56,200 mPa·s and an amine number of 0.84 was obtained. High-resolution $^{29}$Si NMR investigations disclosed no block structures of the (aminopropyl)methylsilyloxy units.

The amounts of starting materials and process parameters are summarized in Table 9b.

TABLE 9b

| | |
|---|---|
| Proportion of polydimethylsiloxane transported | 80.0% by vol. |
| Proportion of (aminoalkyl)silane hydrolysis product transported | 8.8% by vol. |
| Proportion of stopper transported | 10.8% by vol. |
| Proportion of catalyst transported | 0.1% by vol. |
| Proportion of deactivator transported | 0.3% by vol. |
| Internal reaction temperature | 130° C. |
| Temperature of thermostating unit for polydimethylsiloxane and (aminoalkyl)silane hydrolysis product | 110° C. |

TABLE 9b-continued

| | |
|---|---|
| Temperature of thermostating unit for Me$_3$Si—(O—SiMe$_2$)$_{140}$—OSiMe$_3$ | 50° C. |
| Reactor pressure | 200 mbar |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A continuous process for the preparation of organopolysiloxanes having chain-pendant aminoalkyl groups, comprising
   (i) reacting
      (A) linear, cyclic or branched organopolysiloxanes, with
      (B) aminoalkylsilanes which have an SiC-bonded, basic nitrogen-containing hydrocarbon radical and 2 or 3 hydrolyzable groups, or the partial or complete hydrolysis products thereof,
      (C) in the presence of at least one basic catalyst selected from the group consisting of alkali metal hydroxides, alkali metal alcoholates, and alkali metal siloxanolates,
      and, optionally,
      (D) chain-terminating reagents, and
   (ii) optionally, after the reaction (i) neutralizing the basic catalysts (C), with the proviso that compounds (A), (B) and, when used, (D) are reacted continuously in a reactor having a reaction space whose ratio of length to diameter is equal to or greater than four,
   and wherein the aminoalkyl groups are randomly distributed in the organopolysiloxane without block structures containing aminoalkyl groups.

2. The process of claim 1, wherein the reaction space is part of a reactor selected from the group consisting of tubular reactors, loop reactors, kneaders, and extruders.

3. The process of claim 1, wherein compounds (A), (B), (C), and optionally (D) are passed continuously through the reaction space and the compounds (A), (B) and, when used, (D) are reacted there, in the presence of the catalyst (C), and the organopolysiloxanes having aminoalkyl groups which are thus obtained are removed continuously from the reaction space.

4. The process of claim 1, wherein the reaction (i) is carried out in the presence of an alkali metal hydroxide catalyst (C).

5. The process of claim 1, wherein the organopolysiloxanes (A) are selected from the group consisting of
   linear polydiorganosiloxanes of the general formula

HOR$_2$SiO(R$_2$SiO)$_x$SiR$_2$OH (I), and

R$_3$SiO(R$_2$SiO)$_y$SiR$_3$ (II), cyclic polydiorganosiloxanes of the general formula

(OSiR$_2$)$_z$ (III), and mixtures thereof,
   in which each R are identical or different monovalent optionally halogenated C$_{1-18}$ hydrocarbon radicals,
   x is 0 or an integer from 1 to 800,
   y is 0 or an integer from 1 to 800, and
   z is an integer from 3 to 12.

6. The process of claim 1, wherein the aminoalkylsilanes (B) are those of the general formula

X$_n$R$_{(3-n)}$SiZ (IV)

and partial or complete hydrolysis products thereof,
   in which
   R are each identical or different monovalent optionally halogenated C$_{1-18}$ hydrocarbon radicals,
   X is a hydrolyzable group selected from the group consisting of OR$^1$, NR'$_2$ and —Cl,
   R$^1$ is a monovalent C$_{1-18}$ alkyl radical, which may be substituted by one or two ether oxygen atoms,
   R' is hydrogen or a monovalent C$_{1-18}$ hydrocarbon radical,
   Z is a monovalent SiC-bonded, basic nitrogen-containing hydrocarbon radical and n is 2 or 3.

7. The process of claim 1, wherein the catalyst (C) is selected from the group consisting of alkali metal alcoholates, alkali metal siloxanolates, and mixtures thereof.

8. The process of claim 1, wherein a chain-terminating reagent (D) is employed, and is selected from the group consisting of monoalkoxysilanes, aminomonoalkoxysilanes, linear and cyclic silazanes, alcohols, short-chain linear diorganopolysiloxanes, and mixtures thereof.

9. The process of claim 1, wherein at least one of long chain carboxylic acids liquid at room temperature, triorganosilyl phosphates, or triorganophosphates are employed as a neutralizing agent (E).

10. The process of claim 1, wherein the process is carried out at a temperature of from 50 to 180°C.

11. The process of claim 1, wherein the average residence time in the reaction space is from 1 to 180 minutes.

12. The process of claim 1, wherein component (B) comprises an at least partly hydrolyzed aminoalkylsilane.

13. The process of claim 1, wherein component (B) comprises
   wherein
   R are identical or different optionally halogenated C$_{1-18}$ hydrocarbon radicals,
   Z is a monovalent SiC-bonded, basic nitrogen-containing hydrocarbon radical, and
   m is an integer from 2 to 50.

14. The process of claim 1, wherein the reaction space contains one or more perforated trays or sieve trays across a width of the reactor.

15. The process of claim 1, wherein the reactor contains a stirrer.

16. The process of claim 1, wherein a triorganophosphate, triorganosilylphosphate or mixture thereof is employed as a neutralizing agent.

* * * * *

UNITED STATES PATENT AND TRADEMARK OFFICE
CERTIFICATE OF CORRECTION

| | | |
|---|---|---|
| PATENT NO. | : 7,939,618 B2 | Page 1 of 1 |
| APPLICATION NO. | : 12/111293 | |
| DATED | : May 10, 2011 | |
| INVENTOR(S) | : Daniel Schildbach et al. | |

It is certified that error appears in the above-identified patent and that said Letters Patent is hereby corrected as shown below:

Column 18, Line 41, Claim 13:

After "comprises" insert -- $HO(ZRSiO)_mH$ --.

Signed and Sealed this

Twenty-third Day of August, 2011

David J. Kappos
*Director of the United States Patent and Trademark Office*